United States Patent
Bunnenberg et al.

(10) Patent No.: US 6,504,060 B1
(45) Date of Patent: Jan. 7, 2003

(54) CONTINUOUS PROCESS FOR THE PREPARATION OF DIAMINODICYCLOHEXYLMETHANE

(75) Inventors: Rolf Bunnenberg, Leichlingen (DE); Andreas Gröschl, Leverkusen (DE); Michael Holzbrecher, Engelskirchen (DE); Andreas Schulze Tilling, League City, TX (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/122,769

(22) Filed: Apr. 15, 2002

(30) Foreign Application Priority Data

Apr. 19, 2001 (DE) .......................................... 101 19 135

(51) Int. Cl.$^7$ ............................................. C07C 204/00
(52) U.S. Cl. ...................................................... 564/451
(58) Field of Search .......................................... 564/451

(56) References Cited

U.S. PATENT DOCUMENTS 5,578,546 A  11/1996  Maschmeyer et al. ...... 639/327

*Primary Examiner*—Samuel Barts
(74) *Attorney, Agent, or Firm*—Joseph C. Gil; Richard E. L. Henderson; Godfried R. Akorli

(57) ABSTRACT

The invention relates to a process for the preparation of diaminodicyclohexylmethane ("PACM") with a proportion of trans,trans-4,4'-diaminodicyclohexylmethane of from 17 to 24% by hydrogenation of diaminodiphenylmethane ("MDA") in the presence of a pulverulent catalyst in a continuously operated suspension reactor at a conversion of MDA of at least 95%, based on the amount of MDA used.

15 Claims, No Drawings

CONTINUOUS PROCESS FOR THE PREPARATION OF DIAMINODICYCLOHEXYLMETHANE

BACKGROUND OF THE INVENTION

The present invention relates to a continuous process for the preparation of diaminodicyclohexylmethane ("PACM") by hydrogenation of diaminodiphenylmethane ("MDA") in the presence of a pulverulent catalyst.

PACM is prepared industrially by hydrogenating MDA. PACM is used, for example, for the preparation of surface coatings, primarily as a precursor for the surface-coating raw material diisocyanatodicyclohexyl-methane. The isomer ratio is of particular importance for a number of applications.

EP 639,403 A2 discloses a catalyst for the preparation of PACM with a low proportion of trans,trans isomer by hydrogenating MDA. This catalyst has a thin ruthenium- or rhodium-containing layer on a special support, namely a calcined or superficially rehydrated transition alumina, particularly hydragillite or bayerite.

EP 639,403 A2 describes the deactivation of the catalyst by higher molecular weight constituents of the reaction mixture and the adjustment of a low proportion of trans,trans isomer in the product as a problem in the industrial preparation of PACM. The use of special catalysts is intended to solve these problems. However, the special catalyst is primarily suitable for use in reactors with a fixed catalyst bed in which the catalyst cannot be exchanged during operation. In addition, a large part of the reactor volume is occupied by the inactive core of the coated catalyst used and is no longer available as reaction volume.

Hydrogenations in discontinuously operated suspension reactors have already been described. This procedure has the disadvantage that in the case of a rapid reaction, the reaction cannot be terminated quickly enough at the end-point of the reaction, i.e., upon complete conversion and simultaneously specified content of trans,trans isomer. There is therefore always the risk that incomplete conversion or product with an undesirably high proportion of trans,trans isomer is obtained. For this reaction procedure, it is thus necessary to generally use catalysts with a lower activity or to work at low temperatures, which leads to long reaction times and a low space-time yield.

An object of the invention was therefore to provide a continuously operable process for the preparation of PACM with a low proportion of trans,trans4,4'-diaminodicyclohexylmethane characterized by a high space-time yield and a high catalyst service life.

Surprisingly, it has been found that the object can be achieved by carrying out the hydrogenation of MDA to PACM in a continuously operated suspension reactor.

SUMMARY OF THE INVENTION

The invention provides a process for the preparation of diaminodicyclohexylmethane ("PACM") with a proportion of trans,trans4,4'-diaminodicyclohexylmethane of from 17 to 24% comprising hydrogenating diaminodiphenylmethane ("MDA") in the presence of a pulverulent catalyst in a continuously operated suspension reactor at a conversion of MDA of at least 95%, based on the amount of MDA.

DETAILED DESCRIPTION OF THE INVENTION

The conversion of MDA is preferably at least 99%, based on the amount of MDA used. The conversion can be influenced by measures known to the person skilled in the art, for example, by adjusting the residence time in the continuously operated suspension reactor.

It is particularly advantageous to use a cascade of two or more serially connected suspension reactors, for example, a cascade of stirred-tank reactors or a cascade of bubble-columns. Preference is given to using a cascade of two or more serially connected suspension reactors consisting of at least three serially connected reactors.

The MDA starting material is mixed with the pulverulent catalyst and the hydrogen required for the hydrogenation when using stirred-tank reactors as the suspension reactors by means of a stirrer and when using bubble-columns as suspension reactors by introducing hydrogen at high speed and generating a turbulent flow within the reactor.

The pulverulent catalyst to be used according to the invention preferably comprises ruthenium, preferably 1 to 10% by weight (particularly preferably 4 to 8% by weight) of ruthenium.

The ruthenium is preferably applied to a support in fine distribution in order to ensure good catalyst service life and good filterability. Suitable supports are, for example, aluminum oxides.

In a particular embodiment, the ruthenium is distributed largely homogeneously over the cross section of the support particles. This ensures that, upon mechanical stress within the reactor, no ruthenium particles are detached from the support, which is readily possible in the case of coated catalysts. Mechanical loading within the reactor sometimes results in breakage of the catalyst particles. In contrast to a coated catalyst, a homogeneously impregnated catalyst does not produce a ruthenium-free surface but instead a fresh active ruthenium-containing catalyst surface.

A catalyst in which the ruthenium is distributed largely homogeneously over the cross section of the support particles can be prepared, for example, by first allowing an aqueous solution of a ruthenium salt (e.g., ruthenium chloride or ruthenium nitrosilyl nitrate) to act upon an aluminum oxide powder and then precipitating out the ruthenium by adding a base (e.g., NaOH).

The catalyst is preferably used as a powder with an average diameter of the catalyst particles of from 5 to 150 $\mu$m, particularly preferably 10 to 120 $\mu$m, particularly preferably 30 to 100 $\mu$m. The catalyst can be used, for example, in an amount of from 1 to 10% by weight (preferably 3 to 8% by weight), based on the reaction mixture.

The process according to the invention is carried out, for example, at a temperature of from 130 to 200° C., preferably from 140 to 190° C., particularly preferably from 150 to 180° C.

When using a cascade reactor, the temperatures of the individual reactors can be different. It is advantageous to choose a temperature in the first reactor that is higher than that in the last reactor. For a cascade of three reactors, the first reactor can be operated at 180° C., the second at 170° C., and the third at 150° C., for example.

The hydrogen pressure is, for example, from 50 to 400 bar, preferably from 100 to 200 bar.

Hydrogen is advantageously added in an excess of from 5 to 200%, preferably from 20 to 100%, of theory.

The process according to the invention can be carried out with or without the addition of organic solvents. Examples of suitable solvents are alcohols, preferably secondary alcohols (e.g., isobutanol, cyclohexanol, or methylcyclohexanol) or tertiary alcohols (e.g., tert-butanol), particularly preferably tertiary alcohols.

After the catalyst has been separated off, the solvent can be separated from the product by distillation and returned to the hydrogenation process.

It is advantageous to keep the content of water in the reaction mixture low since water results in deactivation of the catalyst. The proportion of water in the reaction mixture is preferably kept lower than 1% by weight, particularly preferably lower than 0.5% by weight.

In the process according to the invention, it is possible to use diaminodiphenylmethane ("MDA") which, in addition to MDA, comprises possible higher molecular weight aromatic amines.

In order to achieve an optimum space-time yield, it is advantageous to bring the reaction mixture to the reaction temperature before it is fed into the continuously operated suspension reactor.

The parameters catalyst concentration, temperature, and residence time in the reactor can be used to adjust the content of trans,trans isomer in the product. In this way, products with a low proportion of trans,trans isomer, particularly with a proportion between 17 and 24%, can be achieved. For example, at a given temperature and catalyst concentration, the proportion of trans,trans isomer in the product can be adjusted by adapting the residence time of the reaction mixture in the reactor.

In the process according to the invention, the catalyst can be conveyed through the reactor or the reactor cascade together with the reaction mixture. The product mixture is then usually cooled, the excess hydrogen is removed, and the catalyst is filtered off. Preferably, after the product solution has been separated off, the catalyst is reused.

With regard to catalyst activity and service life, it is advantageous to wash the catalyst with a solvent after the product solution has been separated off, which enables the catalyst surface to be freed from deposits of higher molecular weight reaction products.

If the catalyst activity decreases after a relatively long period of operation, some of the catalyst can be removed from the system and replaced by fresh catalyst, meaning that a plant for carrying out the process according to the invention can be operated with constant average catalyst activity and constant throughput.

The invention is illustrated in more detail below by reference to examples. The examples represent individual embodiments of the invention, but the invention is not limited to the examples. Those skilled in the art will readily understand that known variations of the conditions of the following procedures can be used. Unless otherwise noted, all temperatures are degrees Celsius and all percentages are percentages by weight.

EXAMPLES

Example 1

The experiment was carried out in a continuously operated stirred tank reactor having a reaction volume of 330 ml. A pulverulent catalyst containing 5% by weight of ruthenium on an $Al_2O_3$ support in a catalyst concentration of 5% by weight was introduced into the stirred-tank reactor. MDA was used in technical-grade quality (so-called MDA 90/10) with a proportion of about 10% of higher molecular weight components as a 33% strength by weight solution in isobutanol. The MDA 90/10-isobutanol mixture was metered into the reactor from a storage container. The reaction pressure was kept constant at 150 bar by continually replenishing hydrogen, and a temperature of 150° C. was set.

The overflow of the reaction mixture passed into another container from which samples were taken for analysis. The samples were analyzed using gas chromatography. By varying the discharge capacity of the dosing pump, various average residence times were set. For comparison, the residence time was set in one case so that the conversion of MDA, based on the amount of MDA used, was only 91.5%. In this case, the proportion of trans,trans isomer of the resulting PACM was below the desired range.

The contents of MDA, $[H_6]$-MDA (i.e., 4-aminocyclohexyl4-amino-phenylmethane), PACM and the proportion of trans,trans-PACM (t,t proportion) are given in Table 1.

TABLE 1

|  | Single-stage stirred-tank reactor | Single-stage stirred-tank reactor | Single-stage stirred-tank reactor (comparison) |
| --- | --- | --- | --- |
| Temperature [° C.] | 150 | 150 | 150 |
| Residence time [min] | 61 | 29 | 12 |
| Throughput [g of PACM per l and h] | 247 | 494 | 715 |
| PACM [%] | 88 | 81 | 48 |
| tt proportion [%] | 24 | 17 | 14 |
| $[H_6]$-MDA [%] | 1.5 | 8.2 | 34 |
| MDA [%] | 0.1 | 0.7 | 8.5 |
| Higher molecular weight components [%] | 10 | 10 | 10 |

Example 2

The experiment was carried out under the same conditions as in Example 1, but the residence time was shortened so that conversion was only partial. The product was then conveyed through the reactor two more times. The product corresponds to the product obtained in a cascade of three stirred-tank reactors.

The contents of MDA, $[H_6]$-MDA, and PACM and the proportion of trans,trans-PACM (t,t proportion) are given in Table 2.

TABLE 2

|  | Single-stage stirred-tank reactor | Three-stage stirred-tank reactor |
| --- | --- | --- |
| Temperature [° C.] | 150 | 150 |
| Residence time [min] | 51 | 45 |
| Throughput [g of PACM per l and h] | 247 | 330 |
| PACM [%] | 88 | 89 |
| tt proportion [%] | 24 | 19 |
| $[H_6]$-MDA [%] | 1.5 | 0.9 |
| MDA [%] | 0.1 | 0.1 |
| Higher molecular weight components [%] | 10 | 10 |

The experiment shows that when a cascade of three reactors is used, a very high conversion of MDA and a trans,trans proportion in the region of 20% can be simultaneously achieved and a high space-time yield is also achieved.

Comparative Example

Discontinuously Operated Stirred-tank Reactor

The experiment was carried out in a discontinuously operated stirred-tank reactor having a reaction volume of 330 ml. A pulverulent catalyst comprising 5% by weight of ruthenium on an $Al_2O_3$ support in a catalyst concentration of 5% by weight was introduced into the stirred-tank reactor. MDA was used in a technical-grade quality (so-called MDA 90/10) with a proportion of about 10% of higher molecular weight components as a 33% strength by weight solution in isobutanol. 330 ml of the MDA 90/10-isobutanol mixture were metered into the reactor from a storage container. The reactor pressure was kept constant at 150 bar by continually replenishing hydrogen, and a temperature of 150° C. was set.

Samples were taken for analysis from the reaction mixture after various residence times of the reaction mixture in the reactor. The samples taken were analyzed using gas chromatography.

The contents of MDA, $[H_6]$-MDA, and PACM and the proportion of trans,trans-PACM (t,t proportion) are given in Table 3.

TABLE 3

|  | Discontinuous stirred-tank reactor | Discontinuous stirred-tank reactor | Discontinuous stirred-tank reactor |
| --- | --- | --- | --- |
| Temperature [° C.] | 150 | 150 | 150 |
| Residence time [min] | 51 | 111 | 171 |
| Throughput [g of PACM per l and h] | 282 | 131 | 81 |
| PACM [%] | 84 | 85 | 81 |
| tt proportion [%] | 14 | 24 | 37 |
| $[H_6]$-MDA [%] | 3.1 | 0.2 | 0.3 |
| MDA [%] | 0.5 | 0.1 | 0 |
| Higher molecular weight components [%] | 12 | 14 | 18 |

The experiment shows that a product with a proportion of 20% trans,trans isomer can be obtained at a significantly lower space-time yield than for continuous hydrogenation in a cascade of three reactors.

What is claimed is:

1. A process for the preparation of diaminodicyclohexylmethane with a proportion of trans,trans4,4'-diaminodicyclohexylmethane of from 17 to 24% comprising hydrogenating diaminodiphenylmethane in the presence of a pulverulent catalyst in a continuously operated suspension reactor at a conversion of diaminodiphenylmethane of at least 95%, based on the amount of diaminodiphenylmethane.

2. A process according to claim 1 wherein the continuously operated suspension reactor is a cascade of two or more serially connected suspension reactors.

3. A process according to claim 2 wherein the cascade of two or more serially connected suspension reactors is a cascade of stirred-tank reactors.

4. A process according to claim 2 wherein the cascade of two or more serially connected suspension reactors is a cascade of bubble-columns.

5. A process according to claim 1 wherein the pulverulent catalyst comprises 1 to 10% by weight of ruthenium.

6. A process according to claim 5 wherein the ruthenium is applied to a support material and is distributed over the entire cross section of the support material.

7. A process according to claim 1 wherein the catalyst is used as a powder with an average diameter of from 5 to 150 $\mu$m.

8. A process according to claim 1 carried out at a temperature of from 130 to 200° C.

9. A process according to claim 1 carried out at a pressure of from 50 to 400 bar is used.

10. A process according to claim 1 carried out in the presence of an alcohol as solvent.

11. A process according to claim 1 wherein the proportion of water in the reaction mixture is less than 1% by weight.

12. A process according to claim 1 wherein the diaminodiphenylmethane additionally comprises higher molecular weight aromatic amines.

13. A process according to claim 1 wherein the pulverulent catalyst is suspended in the diaminodiphenylmethane and the resultant mixture is brought to the reaction temperature before being fed into the continuously operated suspension reactor.

14. A process according to claim 1 wherein the diaminodicyclohexylmethane is separated from the catalyst and the separated catalyst is washed with a solvent.

15. A process according to claim 1 wherein the diaminodicyclohexylmethane is separated from the catalyst and the separated catalyst is reused.

* * * * *